(12) United States Patent
Palese

(10) Patent No.: US 12,239,308 B2
(45) Date of Patent: Mar. 4, 2025

(54) ANCHORING SYSTEM AND METHOD FOR SECURING A SUTURE TO A PRE-DRILLED BORE

(71) Applicant: BIOMET SPORTS MEDICINE, LLC, Warsaw, IN (US)

(72) Inventor: Christopher M. Palese, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 154 days.

(21) Appl. No.: 16/630,234

(22) PCT Filed: Jul. 13, 2018

(86) PCT No.: PCT/US2018/042032
§ 371 (c)(1),
(2) Date: Jan. 10, 2020

(87) PCT Pub. No.: WO2019/014557
PCT Pub. Date: Jan. 17, 2019

(65) Prior Publication Data
US 2020/0155140 A1    May 21, 2020

Related U.S. Application Data

(60) Provisional application No. 62/592,896, filed on Nov. 30, 2017, provisional application No. 62/532,705, filed on Jul. 14, 2017.

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0409* (2013.01);
(Continued)

(58) Field of Classification Search
CPC ........ A61B 17/0401; A61B 2017/0409; A61B 2017/0412; A61B 2017/0414;
(Continued)

(56) References Cited

U.S. PATENT DOCUMENTS 6,306,159 B1 * 10/2001 Schwartz ........... A61B 17/0401
606/232
7,572,283 B1 * 8/2009 Meridew ............... A61F 2/0805
606/328

(Continued)

FOREIGN PATENT DOCUMENTS

CA       2995787 A1     8/2018
CN     111050669 A     4/2020
(Continued)

OTHER PUBLICATIONS

"International Application Serial No. PCT/US2018/042032, International Search Report mailed Oct. 24, 2018", 8 pgs.
(Continued)

*Primary Examiner* — Brigid K Byrd
(74) *Attorney, Agent, or Firm* — Schwegman Lundberg & Woessner, P.A.

(57) ABSTRACT

An anchoring system (11) including a suture anchor (10) and an implant delivery device (22) is disclosed. The suture anchor (10) includes an anchor body (12) and a distal member (14) that is rotatable relative to the anchor body (12) about a longitudinal suture anchor axis. The distal member (14) has an aperture (15) that traverses the distal member (14) and includes a slot (56) and an eyelet (16), the eyelet (16) being sized to permit a suture (20) to traverse the distal member (14) through the eyelet (16). The implant delivery device (22) includes a handle portion (28), a drive shaft portion (6) including a cannulated outer shaft (24), and a suture pulley shaft (8) including an inner shaft (26). The cannulated outer shaft (24) is configured to engage a proxi-
(Continued)

mal end of the anchor body (12) for driving the suture anchor (10) into a bore. The inner shaft (26) is slidably received in the cannulated outer shaft (24) to maintain the position and tension of the sutures (20) during insertion.

18 Claims, 11 Drawing Sheets

(52) U.S. Cl.
CPC .............. *A61B 2017/0412* (2013.01); *A61B 2017/0414* (2013.01); *A61B 2017/044* (2013.01); *A61B 2017/0496* (2013.01); *A61F 2002/0852* (2013.01)

(58) Field of Classification Search
CPC ...... A61B 2017/044; A61B 2017/0496; A61B 2017/0427; A61B 2017/0448; A61B 2017/0445; A61B 2017/0446; A61B 2017/0438; A61B 2017/0433; A61B 17/8685; A61B 2017/0456; A61F 2/0811; A61F 2002/0852; A61F 2002/0823
See application file for complete search history.

(56) References Cited

U.S. PATENT DOCUMENTS

| | | | |
|---|---|---|---|
| 9,770,324 B2 * | 9/2017 | Trenhaile | A61F 2/0811 |
| 2004/0138706 A1 | 7/2004 | Abrams et al. | |
| 2008/0009904 A1 * | 1/2008 | Bourque | A61B 17/0401 606/232 |
| 2009/0312794 A1 | 12/2009 | Nason et al. | |
| 2010/0069958 A1 * | 3/2010 | Sullivan | A61B 17/0642 606/232 |
| 2011/0276092 A1 * | 11/2011 | Dreyfuss | A61B 17/0401 606/232 |
| 2012/0165868 A1 * | 6/2012 | Burkhart | A61B 17/0401 606/232 |
| 2013/0006302 A1 * | 1/2013 | Paulk | A61F 2/0811 606/232 |
| 2013/0103083 A1 * | 4/2013 | Baird | A61B 17/0401 606/232 |
| 2013/0197578 A1 * | 8/2013 | Gregoire | A61B 17/0401 606/232 |
| 2014/0277128 A1 | 9/2014 | Moore et al. | |
| 2014/0364906 A1 * | 12/2014 | Palese | A61B 17/0401 606/232 |
| 2015/0018878 A1 * | 1/2015 | Rizk | A61L 31/127 606/232 |
| 2016/0066900 A1 * | 3/2016 | Brunsvold | A61B 17/0401 606/232 |
| 2016/0338689 A1 | 11/2016 | Baird | |
| 2018/0235746 A1 * | 8/2018 | Pilgeram | A61F 2/0811 |
| 2018/0338755 A1 * | 11/2018 | Palese | A61B 17/0401 |

FOREIGN PATENT DOCUMENTS

| | | | |
|---|---|---|---|
| EP | 3375380 | A2 | 9/2018 |
| EP | 3651657 | B1 | 3/2024 |
| JP | 2006515203 | A | 5/2006 |
| JP | 2020527435 | A | 9/2020 |
| WO | WO-2013052128 | A1 | 4/2013 |
| WO | WO-2013114347 | A1 | 8/2013 |
| WO | WO-2019014557 | A1 | 1/2019 |

OTHER PUBLICATIONS

"International Application Serial No. PCT/US2018/042032, Written Opinion mailed Oct. 24, 2018", 10 pgs.
"Australian Application Serial No. 2018300174, First Examination Report mailed Jun. 10, 2020", pgs.
"Australian Application Serial No. 2018300174, Response filed Jan. 18, 2021 to First Examination Report malled Jun. 10, 2020", 17 pgs.
"Australian Application Serial No. 2018300174, Response filed May 24, 2021 to Subsequent Examiners Report mailed Feb. 12, 2021", 18 pgs.
"Australian Application Serial No. 2018300174, Subsequent Examiners Report mailed Feb. 12, 2021", 4 pgs.
"Canadian Application Serial No. 3,069,688, Office Action mailed Mar. 26, 2021", 5 pgs.
"Canadian Application Serial No. 3,069,688, Response filed Jul. 26, 2021 to Office Action mailed Mar. 26, 2021", 21 pgs.
"European Application Serial No. 18749254.1 Response to Communication pursuant to Rules 161(1) and 162 EPC filed Sep. 7, 2020", 17 pgs.
"European Application Serial No. 18749254.1, Communication Pursuant to Article 94(3) EPC mailed Mar. 26, 2021", 7 pgs.
"European Application Serial No. 18749254.1, Response filed Sep. 24, 2021 to Communication Pursuant to Article 94(3) EPC mailed Mar. 26, 2021", 56 pgs.
"International Application Serial No. PCT/US2018/042032, International Preliminary Report on Patentability mailed Jan. 23, 2020", 12 pgs.
"Japanese Application Serial No. 2020-523232, Notification of Reasons for Rejection mailed Apr. 6, 2021", w/ English Translation, 6 pgs.
"Japanese Application Serial No. 2020-523232, Response filed Jun. 21, 2021 to Notification of Reasons for Rejection mailed Apr. 6, 2021", w/ English claims, 16 pgs.
"Chinese Application Serial No. 201880057553.7, Office Action mailed Aug. 16, 2022", w/ English translation, 19 pgs.
"Chinese Application Serial No. 201880057553.7, Response filed Nov. 23, 2022 to Office Action mailed Aug. 16, 2022", w/ English claims, 12 pgs.
"Chinese Application Serial No. 201880057553.7, Office Action mailed Mar. 11, 2023", W/English Translation, 7 pgs.
"Chinese Application Serial No. 201880057553.7, Response filed Apr. 18, 2023 to Office Action mailed Mar. 11, 2023", w/ English claims, 10 pgs.

* cited by examiner

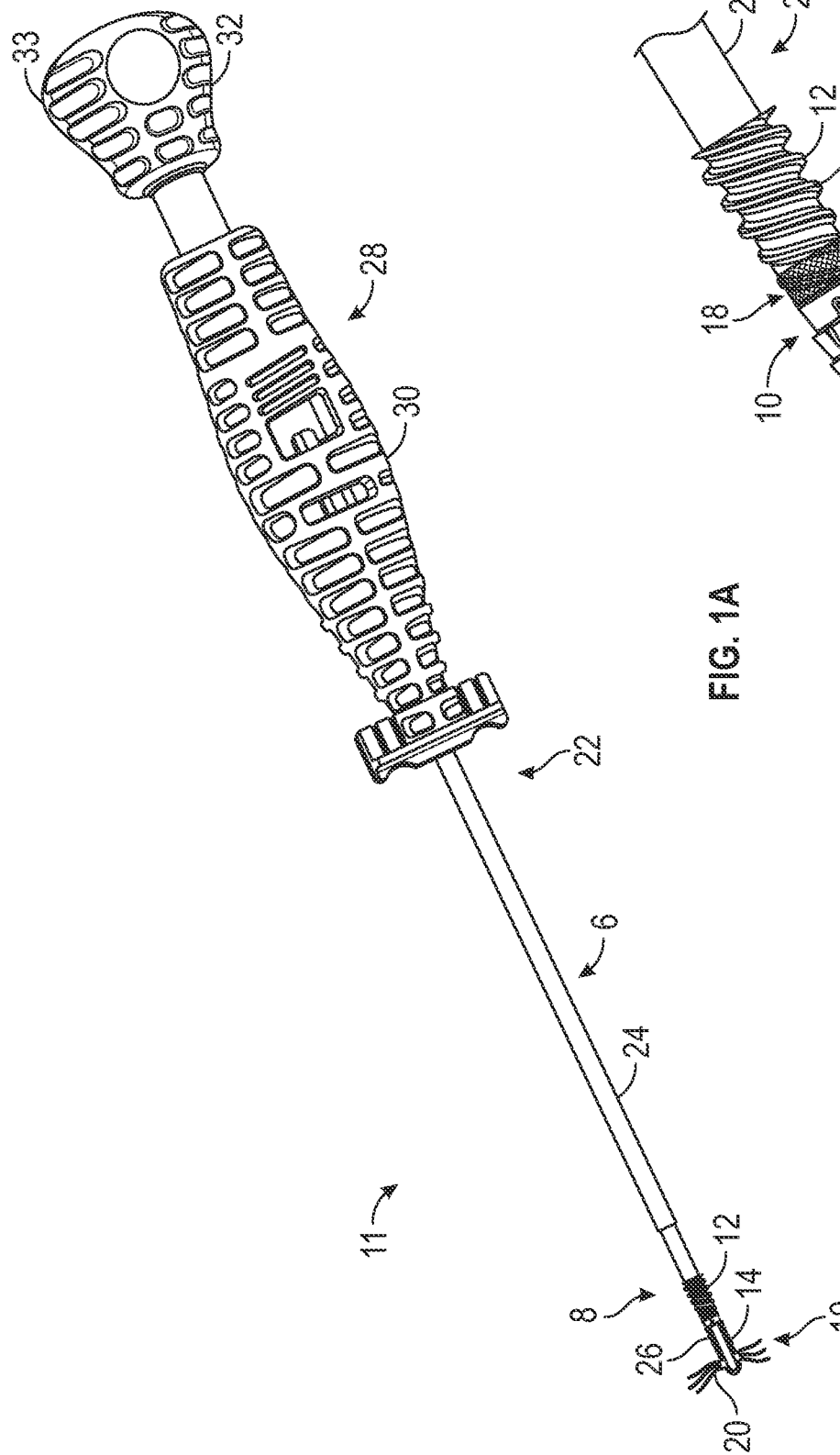
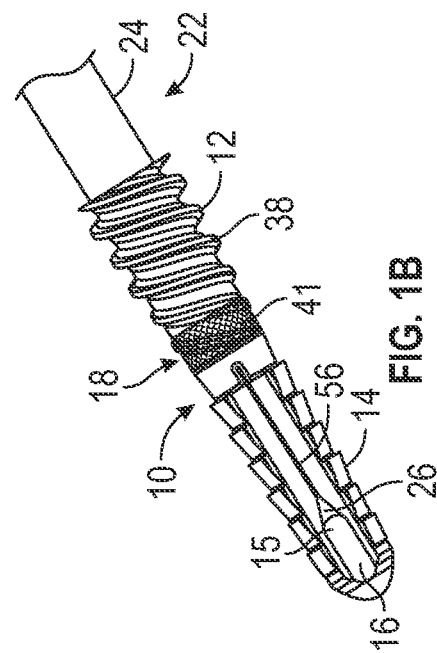
FIG. 1A
FIG. 1B

ANCHORING SYSTEM AND METHOD FOR SECURING A SUTURE TO A PRE-DRILLED BORE

CLAIM OF PRIORITY

This application is a U.S. National Stage Application under 35 U.S.C. 371 from International Application Serial No. PCT/US2018/042032, filed on Jul. 13, 2018, and published as WO 2019/014557 A1 on Jan. 17, 2019, which claims the benefit of U.S. Provisional Patent Application Ser. No. 62/532,705, filed on Jul. 14, 2017, and also claims the benefit of U.S. Provisional Patent Application Ser. No. 62/592,896, filed on Nov. 30, 2017, the benefit of priority of each of which is claimed hereby, and each of which are incorporated by reference herein in its entirety.

FIELD OF THE DISCLOSURE

The present disclosure relates to surgical implant systems, including implants, delivery instruments, and methods for installing an implant. Specifically, the present disclosure relates to an anchoring system including knotless implants, also referred to as suture anchors, for securing soft tissue to bone.

BACKGROUND

Various implant systems have been created for repairing soft-tissue damage in different surgical contexts. As an example, suture anchors have been utilized to repair tears to a tear in a patient's rotator cuff, a patient's labrum in the shoulder or hip, or a tear to a patient's meniscus in the knee. In some cases, the suture anchor is driven into a pre-drilled bone hole, and suture is passed through the particular soft tissue in order to tension the suture construct and draw the tissue back into its normal anatomical position against the bone. At the end of the repair, a knot can be used to assist in drawing the torn soft tissue back to its anatomically-correct position and/or to secure the tissue in position. However, the use of knots to repair soft-tissue tears can result in a number of issues for the patient. For example, knot migration can occur after the initial repair whereby the position of the knot moves during normal physical motion by the patient. In the case of a labrum repair in the shoulder, for example, if the knot migrates far enough, it can become interposed between the glenoid and the humerus and potentially cause chondral abrasion and discomfort or more serious issues for the patient. Further, knot loosening can also occur resulting in an ineffective repair causing the soft tissue to move out of position and not heal correctly.

Knotless suture anchors have also been developed, but such anchors suffer from deficiencies in securing the suture relative to the anchor. Often, a friction-lock is used in which the suture is pressed against the anchor in an attempt to secure the suture relative to the anchor. Of course, such constructs can suffer from slippage and loss of tension between the suture and the anchor at the point of the friction-lock.

The presently disclosed subject matter seeks to address numerous issues with knotted and knotless suture anchors by proving improved knotless implants, instruments, and methods.

SUMMARY

To better illustrate the system disclosed herein, a non-limiting list of examples is provided here:

Example 1 is an anchor system including a suture anchor including an anchor body including a threaded outer surface and a distal member that is rotatable relative to the anchor body about a longitudinal suture anchor axis, the distal member having an aperture that traverses the distal member, the aperture including an eyelet and a slot, the eyelet and the slot being sized to permit a suture to traverse the distal member.

In Example 2, the subject matter of Example 1 optionally includes where the slot has a first slot end positioned toward the proximal end of the distal member and a second slot end positioned adjacent to the eyelet.

In Example 3, the subject matter of Example 2 optionally includes where the eyelet extends from a first eyelet end adjacent to the second slot end to a second eyelet end positioned adjacent to a distal end of the distal member.

In Example 4, the subject matter of Example 3 optionally includes where the slot and the eyelet are in fluid communication with each other and the first slot end is a closed end.

In Example 5, the subject matter of any one or more of Examples 1-4 optionally includes where the aperture defines first and second openings in first and second sides of the distal member through which the suture can extend.

In Example 6, the subject matter of any one or more of Examples 1-5 optionally includes where a maximum dimension of the eyelet is greater than a maximum dimension of the slot.

In Example 7, the subject matter of any one or more of Examples 1-6 optionally includes where the eyelet includes a transition region that permits movement of the suture from the eyelet to the slot.

In Example 8, the subject matter of any one or more of Examples 1-7 optionally includes where the anchor body defines a bore extending from a proximal end of the anchor body to a distal end of the anchor body, wherein the bore defines a stop surface.

In Example 9, the subject matter of Example 8 optionally includes where the distal member includes a suture body portion and a coupling portion, the coupling portion extending from the suture body portion and configured to be received within the bore of the anchor body.

In Example 10, the subject matter of Example 9 optionally includes where the distal member includes a blind bore extending from the coupling portion and terminating within the suture body portion.

In Example 11, the subject matter of any one or more of Examples 1-10 optionally includes an implant delivery device, including: a handle portion; and a drive shaft portion, including: a cannulated outer shaft, the cannulated outer shaft configured to engage a proximal end of the anchor body for driving the suture anchor into a bore; and a suture pulley shaft portion, including: an inner shaft slidably received in the cannulated outer shaft, wherein a distal end of the inner shaft is extendable distally beyond a distal end of the cannulated outer shaft such that, when the cannulated outer shaft is engaging the proximal end of the anchor body, the distal end of the inner shaft is extendable through the anchor body to a distance beyond the distal end of the anchor body to engage with the distal member to rotationally lock the distal member to the inner shaft.

In Example 12, the subject matter of any one of claims 1 through 11 optionally includes wherein, when the suture is tensioned, the tension rotationally locks the inner shaft and distal member relative to the cannulated outer shaft and the anchor body.

In Example 13, the subject matter of any one of claims 1 through 12, where the inner shaft includes a fork on the distal end of the inner shaft.

In Example 14, the subject matter of Example 13 optionally includes where the fork is a two-pronged fork.

In Example 15, the subject matter of any one of Examples 1 through 14 optionally include where the anchoring system is configured so that the suture is at a proper location to be tensioned when the distal end of the inner shaft is on a bottom surface of the bore and holding the suture at a distal positon of the bore.

In Example 16, the subject matter of any one of Examples 1 through 15 optionally include where the anchor body includes an etch line, and wherein a length of the slot is equal to or greater than a length of the anchor body from the proximal end of the anchor body to the proximal end of the etch line.

Example 17 is an anchoring system including a suture anchor including: an anchor body and a distal member that is rotatable relative to the anchor body about a longitudinal suture anchor axis, the distal member having an aperture that traverses the distal member, the aperture including a slot and an eyelet; and an implant delivery device, including: a handle portion; a drive shaft portion, including: a cannulated outer shaft, the cannulated outer shaft configured to engage a proximal end of the anchor body for driving the suture anchor into a bore; and a suture pulley shaft portion, including: an inner shaft slidably received in the cannulated outer shaft, wherein a distal end of the inner shaft is extendable distally beyond a distal end of the cannulated outer shaft such that, when the cannulated outer shaft is engaging the proximal end of the anchor body, the distal end of the inner shaft is extendable through the anchor body to a distance beyond the distal end of the anchor body to engage with the distal member to rotationally lock the distal member to the inner shaft.

In Example 18, the subject matter of Example 17 optionally includes where the anchor body defines a bore extending from a proximal end of the anchor body to a distal end of the anchor body, a portion of the bore having an anti-rotational shape.

In Example 19, the subject matter of one or more of Example 17 or Example 18 optionally includes where the cannulated outer shaft includes a shoulder and an anti-rotational feature extending from the shoulder at a distal end, the anti-rotational feature matching the anti-rotational shape of the bore of the anchor body to rotationally lock the anchor body to the cannulated outer shaft, and wherein the shoulder is configured to engage a proximal end of the anchor body.

Example 20 is a method for securing a suture to a bore, including passing a suture through soft tissue of a patient and through an eyelet of a suture anchor, the suture anchor including: an anchor body and a distal member that is rotatable relative to the anchor body about a longitudinal suture anchor axis, the distal member including the aperture; positioning the suture anchor at a bore so that a portion of the suture distally past the distal end of the anchor body is located at or near a bottom of the bore while the anchor body is above the bore; advancing the suture anchor until a portion of the anchor body is within the bore; tensioning a free end of the suture; and rotating the anchor body via a handle to advance the suture anchor into the bore to secure the suture, wherein the anchor body rotates relative the distal body such that, as the anchor body rotates, a rotational position of the distal member is maintained during insertion.

In Example 21, the subject matter of Example 20 optionally includes mounting the suture anchor to an implant delivery device, the implant delivery device including: a cannulated outer shaft, the cannulated outer shaft including a distal end configured to engage a proximal end of the anchor body for driving the suture anchor into a bore; and an inner shaft slidably received in the cannulated outer shaft, wherein a distal end of the inner shaft is extendable distally beyond the distal end of the cannulated outer shaft such that, when the distal end of the cannulated outer shaft is engaging the proximal end of the anchor body, the distal end of the inner shaft is extendable through the anchor body to a distance beyond the distal end of the anchor body to engage the suture.

In Example 22, the subject matter of Example 21 optionally includes where the distal member includes an aperture that traverses the distal member, the aperture including a slot and the eyelet, wherein, as the suture anchor is advanced into the bore, a distance between the distal end of the inner shaft and the distal end of the cannulated outer shaft decreases thereby inserting the suture anchor and the suture moves from the eyelet into the slot.

In Example 23, the subject matter of Example 22 optionally includes where a distance between the distal end of the inner shaft and the distal end of the cannulated outer shaft decreases simultaneously as the suture moves form the eyelet into the slot.

In Example 24, the subject matter of any one or more of Examples 20 through 23 optionally include where the anchor body includes an etch line located a distance from a proximal end of the anchor body.

In Example 25, the subject matter of any one or more of Examples 20 through 24 optionally include where rotating the anchor body is done after the suture anchor has been inserted into the bore such that that etch line is at or below a surface of the bore.

In Example 26, the subject matter of any one or more of Examples 20 through 25 optionally include where the tension on the suture rotationally locks the inner shaft and the distal member relative the anchor body as the anchor body is rotated via a rotational force.

Example 27 includes a method for securing a suture to a bore including passing a suture through soft tissue of a patient and through an eyelet of a suture anchor, the suture anchor including: an anchor body and a distal member that is rotatable relative to the anchor body about a longitudinal suture anchor axis, the distal member including the aperture; positioning the suture anchor at a bore so that a portion of the suture distally past the distal end of the anchor body is located at or near a bottom of the bore while the anchor body is above the bore; tensioning a free end of the suture; advancing the suture anchor, after tensioning, until a portion of the anchor body is within the bore; and rotating the anchor body via a handle to advance the suture anchor into the bore to secure the suture, wherein the anchor body rotates relative the distal body such that, as the anchor body rotates, a rotational position of the distal member is maintained during insertion.

Each of these non-limiting examples can stand its own, or can be combined in various permutations or combinations with one or more of the other examples

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein:

FIG. 1A illustrates an anchor delivery system including a suture anchor and am implant delivery device in accordance with an example of the disclosure.

FIG. 1B illustrates the anchor of FIG. 1A attached to the implant delivery device.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

Figure 2A:
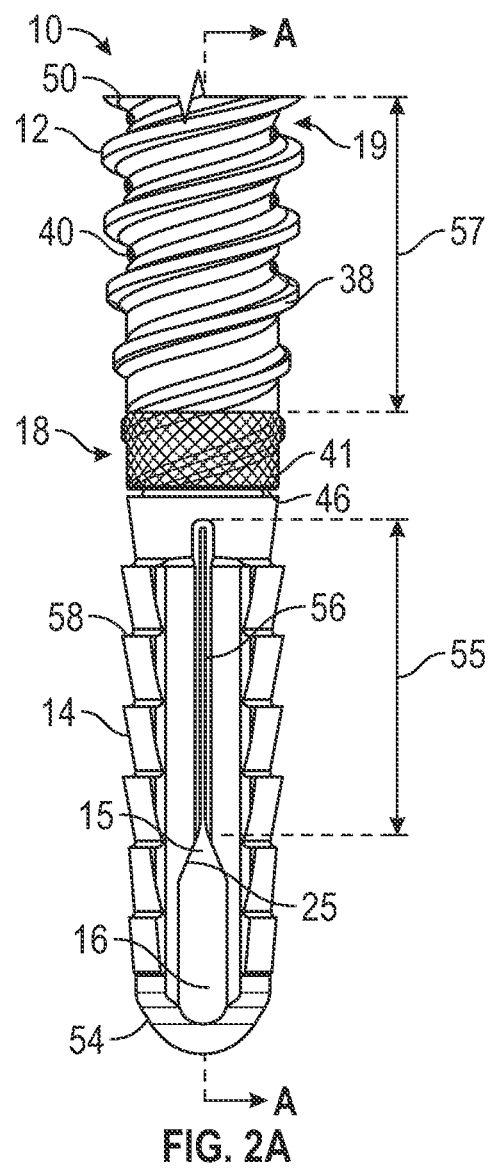
FIG. 2A illustrates a side view of the suture anchor of FIG. 1A without the implant delivery device attached.

In describing the examples of the presently-disclosed subject matter illustrated and to be described with respect to the drawings, specific terminology will be used for the sake of clarity. However, the disclosure is not intended to be limited to any specific terms used herein, and it is to be understood that each specific term includes all technical equivalents.

During a surgical process, a surgeon can prepare one or more bores in a bone. The surgeon can affix sutures to the bone at each bore. For each hole, the surgeon can deploy a implant such as a suture anchor (also referred to as "anchor") into the bore, which can secure the suture between the threads of the suture anchor and the wall of the bore. The devices and methods discussed herein pertain to the suture anchor, the elements used in an implant delivery device that can deploy the suture anchor, and a method of deploying the anchor.

FIG. 1A shows a perspective view of an anchoring system 11 including a knotless implant or suture anchor 10 and an implant delivery device 22. FIG. 1B shows a close-up of the anchor 10 attached to the implant delivery device 22. Suture anchor 10 can be used in various surgical procedures, including repairing soft-tissue tears. Merely as examples, anchor 10 can be used to repair tears of the labrum in the hip or shoulder, tears of the meniscus in the knee, rotator cuff tears, or soft- tissue tears in the small bones, such as in the hand or foot (e.g., collateral ligament repair, scapholunate repair, etc.). Stated another way, anchor 10 can be used in any context where soft tissue is to be fixed to bone for proper reattachment. As anchor 10 is a knotless anchor, it does not suffer from many of the deficiencies associated with soft-tissue repairs that utilize a knot. In addition, anchor 10 can include an improved mechanism for securing suture relative to the suture anchor 10.

The suture anchor 10 includes an anchor body 12 and a distal member 14 located at a distal end 18 of the anchor body 12. The distal member 14 can include an aperture 15 including an eyelet 16 and a slot 56 that can receive one or more sutures 20. As discussed herein, the anchor body 12 and the distal member 14 can rotate independently of each other. Suture(s) 20 are initially be threaded through the eyelet 16 and positioned within the eyelet 16 for a portion of insertion of the suture anchor 10 into a prepared bone hole. During insertion, after the sutures 20 have been tensioned, the sutures 20 can move from the eyelet 16 into the slot 56, which can provide increased coupling between the suture anchor 10 and the sutures 20 and reduce the risk of the suture slipping. For example, the sutures 20 being engaged within the slot 56 can provide additional suture "cleat" fixation.

The implant delivery device 22 includes a drive shaft portion 6 including a cannulated outer shaft 24, a suture pulley shaft portion 8 including an inner shaft 26, and a handle portion 28 including a distal handle 30 and a proximal handle 32 including a turning knob 33. The implant delivery device 22 can be used to deploy the suture anchor 10 into a prepared bone hole.

Referring now to FIGS. 2A-C and 3A-B, which show perspective and cross-sectional views of the suture anchor 10. The anchor body 12 can extend from a proximal end 19 including a proximal surface 50 to a distal end 18 including a distal surface 46. The anchor body 12 can have an outer surface including threads 38 and a portion of the outer surface including a marking, e.g., an etch mark 41. As discussed herein, during insertion, the suture anchor 10 can be inserted (non-rotationally) until the top of the etch mark 41 is at or below a bone surface before tensioning the sutures and advancing the suture anchor 10 to the final placement via rotational force. In one example, a length 55 of the slot 56 can be equal to or greater than a length 57 from the proximal end of the etch mark 41 to the proximal end 19 of the anchor body 12. This reduces the risk that the suture is not over tensioned as the suture anchor 10 is inserted.

Although threads 38 are shown, any alternative advancement and fixation mechanisms can be used alone or in combination, including for example, knurled or ridged surfaces, roughened surfaces, ribs, circumferential grooves extending around part or the entire circumference of the anchor body 12, or the like. Additionally, the anchor body 12 can also include fenestrations 40 to receive bone/tissue during insertion and to assist with osseointegration as the bone heals around the suture anchor 10.

The anchor body 12 can define a bore 36 that extends through the anchor body 12 from the proximal end 19 to the distal end 18. The bore 36 can define a stop surface 42 (FIG. 3A-B) that engages with a surface of the distal member 14 when coupled, as discussed herein. A portion of the bore 36 proximal to the stop surface 42 can include anti-rotational features 44 (see FIG. 2B) that match anti-rotational features of the cannulated outer shaft 24 such that a rotational force can be transferred from the cannulated outer shaft to the anchor body 12.

The anchor 10 includes a distal member 14 that is rotatable relative to the anchor body 12. The distal member 14 is shown with projections 58 that act to provide an outward force sufficient to penetrate the walls of the bore (bone hole) as to prevent the suture anchor 10 from backing of the bore. While projections 58 are shown, any fixation mechanism can be used such as bars, spikes, or the like. Additionally, the distal member 14 can be free from projections, barbs, spikes, or the like and have a substantially smooth outer surface free from fixation mechanisms.

Figure 2B:
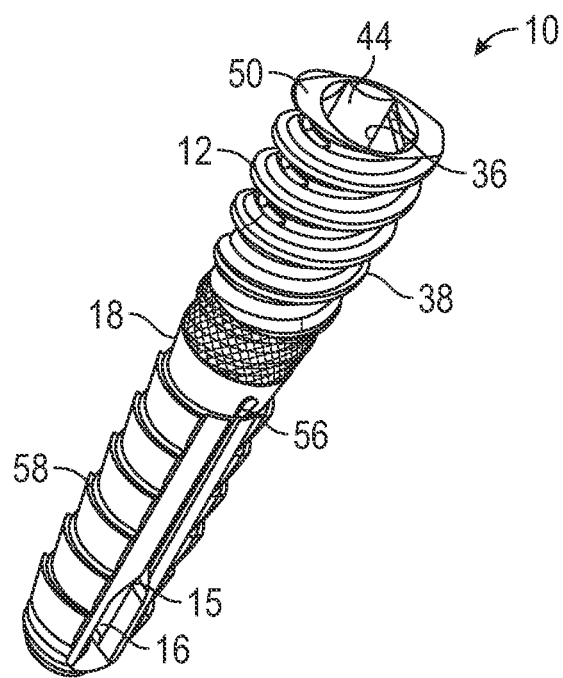
FIG. 2B illustrates a perspective view of the suture anchor in FIG. 2A.
Figure 3B:
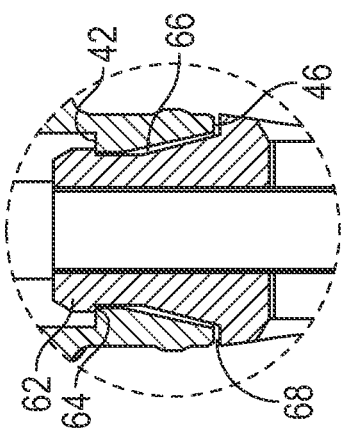
FIG. 3B is a close-up of a portion of the suture anchor in FIG. 3A.
Figure 3A:
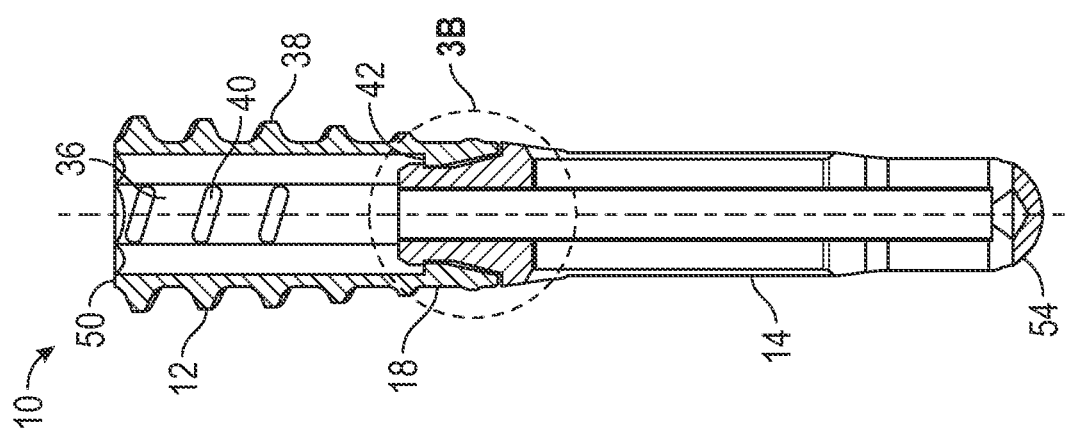
FIG. 3A illustrates a cross-sectional view of the suture anchor in FIG. 2A along cut line A-A.
Figure 2C:
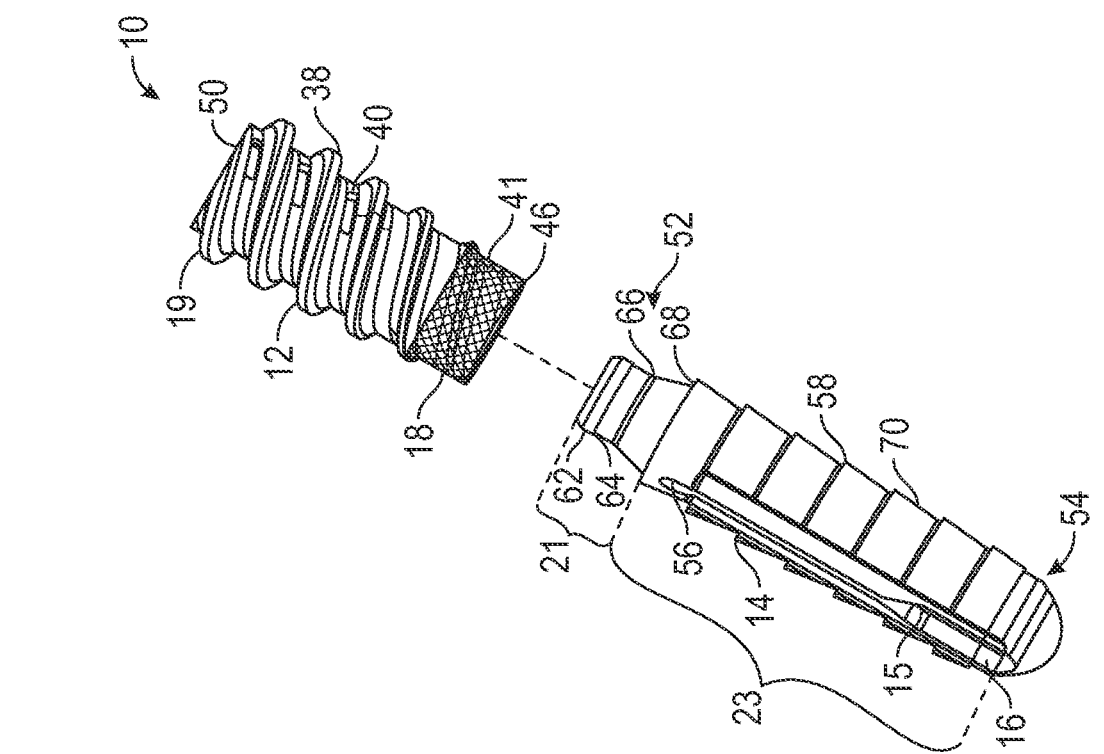
FIG. 2C illustrates an expanded view of the suture anchor of FIGS. 2A and 2B.

As seen in FIGS. 2C, 3A, and 3B, the distal member 14 can extend from a proximal end 52 to a distal end 54 and include a coupling portion 21 and a suture portion 23. The coupling portion 21 is configured to be received within the anchor body 12 and a suture portion 23 is configured to receive and allow movement of one or more sutures within the distal member 14. The distal member 14 includes an aperture 15 that is sized to receive the one or more sutures.

The aperture 15 includes an eyelet 16 and a slot 56. The eyelet 16 can have a maximum cross-sectional dimension and slot can also have a maximum cross-sectional dimension, where the maximum dimension of the slot 56 is smaller than that of the eyelet 16. The eyelet 16 can include a transition portion 25, which is a tapered surface that is adjacent to the slot 56. As discussed herein, the one or more sutures are initially threaded into the eyelet 16 and during insertion can move from the eyelet 16 to the slot 56 to provide additional fixation of the sutures to the suture anchor 10. The transition portion 25 enables the sutures to move from the eyelet 16 to the slot 56. Collectively, eyelet 16 and slot 56 define the aperture 15 that extends through the distal member 14. The transition portion 25 of the eyelet 16 can have a maximum cross-sectional dimension that transitions to a minimum cross-sectional dimension adjacent to the slot 56. This difference in dimension along the transition portion 25 can act to create a neck region between the eyelet 16 and the slot 56 causing the sutures to move towards and into the slot 56 during deployment of suture anchor 10. As the suture anchor 10 is advanced into the bone hole, the sutures 20 move into the slot 56. For example, the inner shaft 26 remains stationary (i.e., fixed translationally) as the outer shaft 24 and suture anchor 10 advance distally causing the slot 56 to move over the sutures 20

The coupling portion 21 can extend from the suture portion 23 such that a shoulder 68 is defined between the coupling and suture portions 21, 23. The coupling portion 21 includes a projection 66 and a lip 62. As seen in FIGS. 3A and 3B, when the distal member 14 is coupled with to the anchor body 12, the projection 66 extends into the bore 36 and the lip 62 is positioned proximal to the stop surface 42 of the bore 36 of the anchor body 12. The diameter of the lip 62 can be larger than a diameter along the stop surface 42. The coupling portion 21 can advance into the bore 36 and until the lip 62 compresses slightly to advance past the stop surface 42. Once the lip 62 advances past the stop surface 42, the lip 62 can expand and a stop surface 64 of the lip 62 engages the stop surface 42 of the bore 36 such that the distal member 14 and the anchor body 12 are coupled. As seen, the cross-sectional shape of the portion of the bore 36 distal to the stop surface 42 of the anchor body 12 can be circular and have a tapered diameter. Generally, the shape and diameter of the portion of the bore 36 matches the shape and diameter of the projection 66 of the coupling portion 21 such that the coupling portion 21 can freely rotate relative the anchor body 12 while coupled to the anchor body 12. A distance between stop surface 64 of the lip 62 and the shoulder 68 can be substantially equal to or greater than the distance between the stop surface 42 of the bore 36 and the distal surface 46 of the anchor body 12.

Figure 4A:
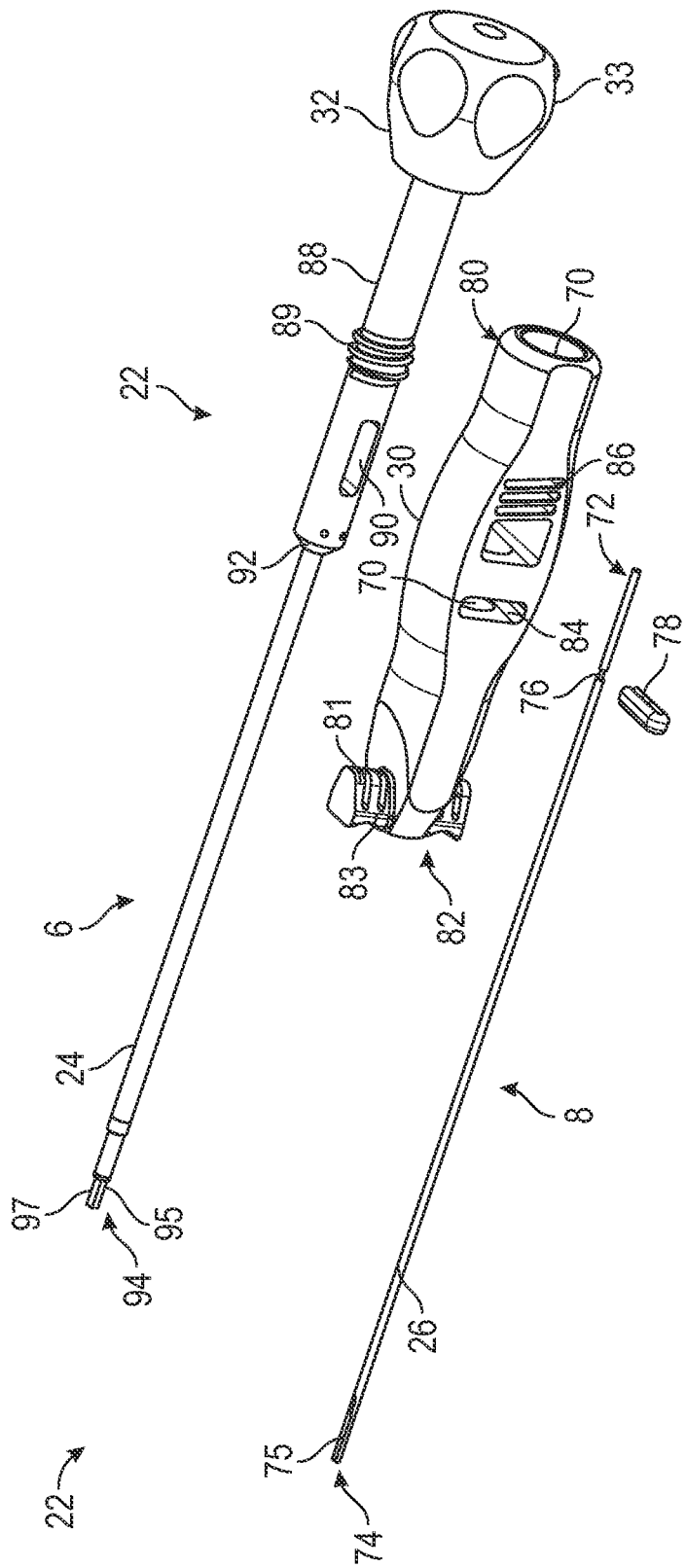
FIG. 4A illustrates an expanded view of the implant delivery device in accordance with an example of the disclosure.
Figure 4B:
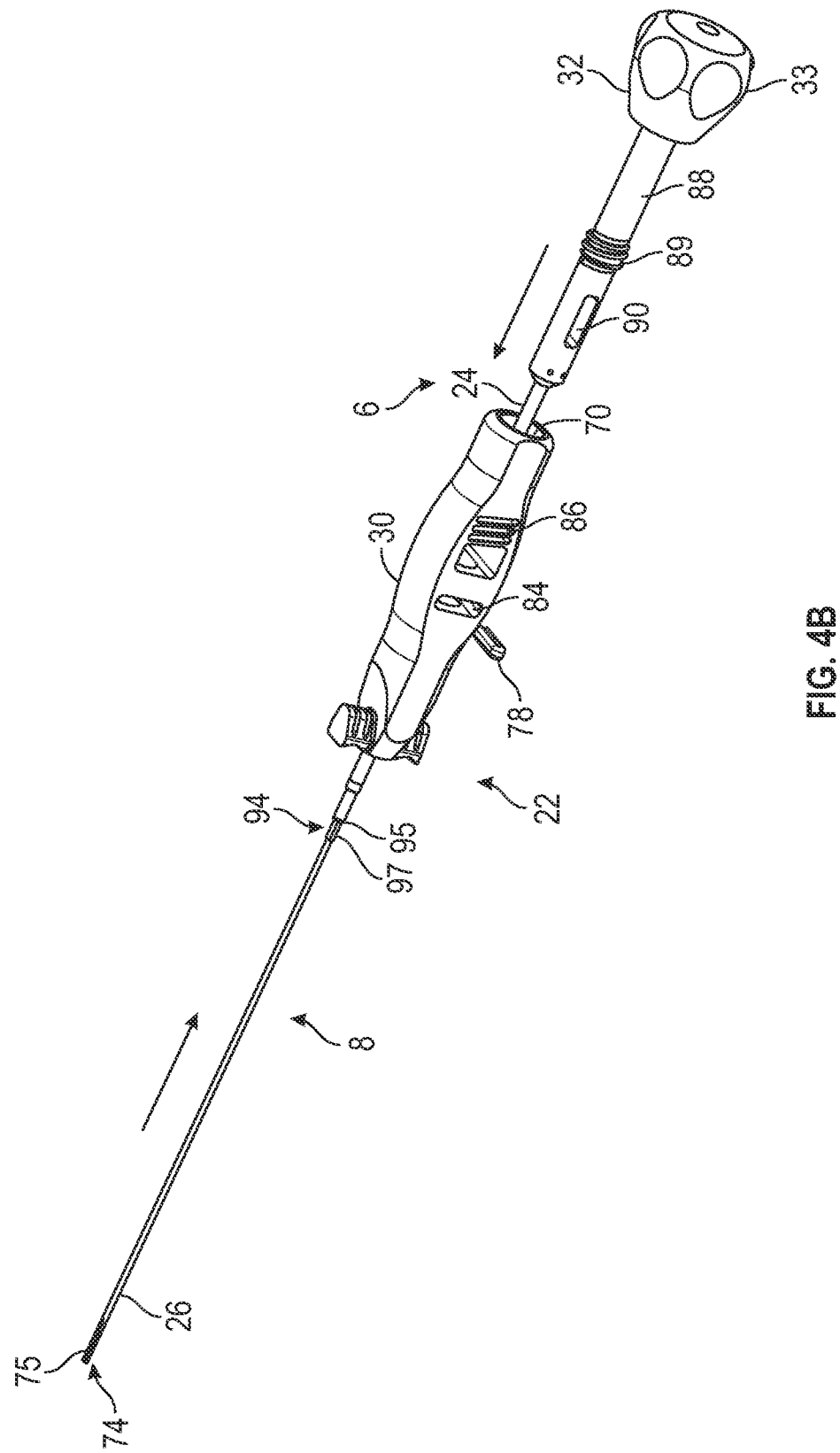
FIG. 4B illustrates a partially expanded view of the implant delivery device in accordance with an example of the disclosure.
Figure 4C:
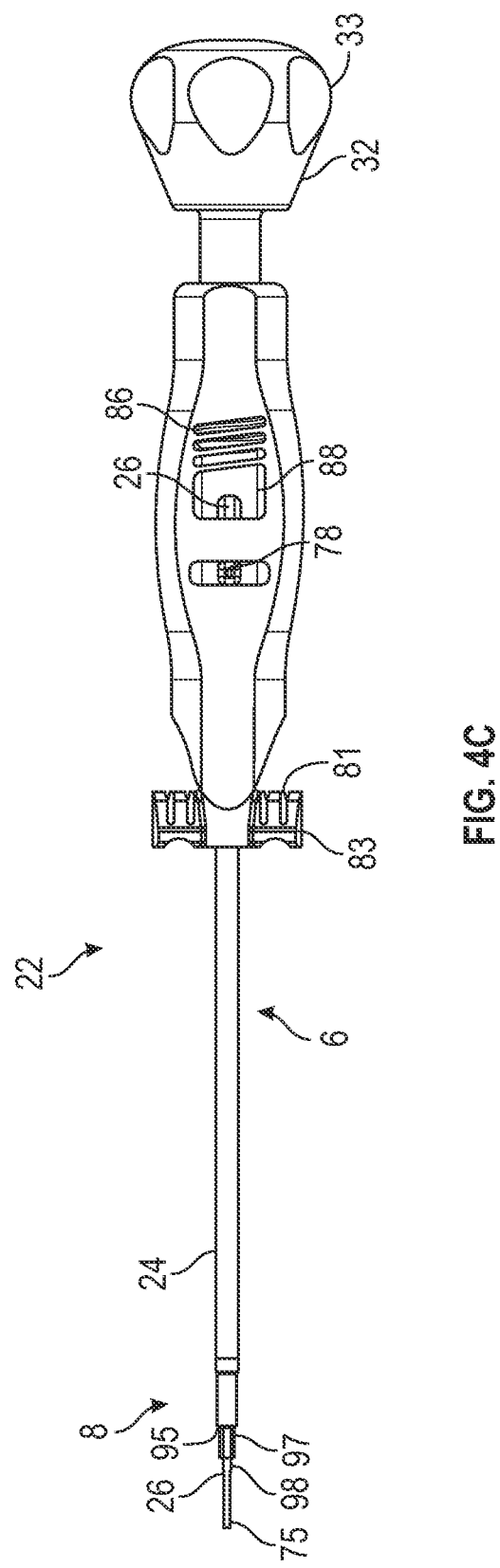
FIG. 4C illustrates a side view of the implant delivery device in accordance with an example of the disclosure.

Implant delivery device 22 is shown in FIGS. 4A-C. The implant delivery device 22 includes the drive shaft portion 6 including the cannulated outer shaft 24, the suture pulley shaft portion 8 including the inner shaft 26, a distal handle 30, and a proximal handle 32. The cannulated outer shaft 24 extends from a proximal end 92 to a distal end 94. The proximal end 92 is coupled to a body 88 of proximal handle 32 such that when a knob 33 of the proximal handle 32 is rotated, the cannulated outer shaft 24 will rotate as well. The cannulated outer shaft 24, the body 88, and the knob 33 can be integral with each other or modular. The distal end 94 of the cannulated outer shaft 24 includes an engagement end 97 that has an anti-rotational feature (e.g., hexagon shape) that matches the anti-rotational feature 44 of the bore 36 of the anchor body 12 (see FIG. 2B). The engagement end 97 has a reduced diameter such that a stop surface 95 is formed and configured to engage the proximal surface 50 of the anchor body 12 when the suture anchor 10 is mounted onto the implant delivery device 22 (see FIG. 6). The body portion 88 includes a window 90 and threads 89. As discussed herein, the threads 89 engage with the distal handle 30 such that as the knob 33 of the proximal handle is rotated, the position of the proximal handle 32 moves relative the distal handle 30.

The distal handle 30 extends from a proximal end 80 to a distal end 82 and defines a bore 70. The distal handle 30 also includes a window 84. The inner shaft 26 extends from a proximal end 72 to a distal end 74, where the distal end 74 includes a fork 75. The inner shaft 26 also includes a groove 76 that can receive a clip 78. Further, the distal handle 30 can include a suture grasper section 83 including cleats 81 that can be used during insertion to assist in suture management after tensioning.

As seen in FIG. 4B, the inner shaft 26 is inserted into the bore 70 at the distal end 82 of the distal handle 30 and the cannulated outer shaft 24 is inserted into the bore 70 at the proximal end 80 of the distal handle 30 such that the cannulated outer shaft 24 extends over the inner shaft 26. When assembled, window 84 of the distal handle 30 and window 90 of the body 88 are aligned and the groove 76 is positioned within window 84 such that the clip can be inserted through the distal handle 30 via window 84 and through the body 88 via window 90 and engage the groove 76 of the inner shaft 26. The clip 78 couples the inner shaft 26 to the distal handle 30 while allowing the proximal handle 32, body 88, and cannulated outer shaft 24 to rotate about the inner shaft 26. For example, when the clip 78 engages the inner shaft 26, the clip 78 extends through the window 90 and within the window 84 extending across the bore 70 such that a translational position of the inner shaft 26 and the distal handle 30 is fixed. Window 90 has a length that is equal to or greater than the length that the proximal handle 32 can move along a longitudinal axis, which is determined by the engagement between the threads 89 on the body 88 and the slots 86 of the proximal handle 30. Once assembled, as the proximal handle 32 is turned, by rotating the knob 33, the clip 78 will engage the edges of the window 90 and rotate within the distal handle 30 and around the inner shaft 26, and allow the inner shaft 26 to maintain the rotational and translational position relative to the distal handle 30. That is, as the clip 78 rotates about the inner shaft 26, the inner shaft 26 is independent from the clip 78 and maintains a fixed rotational and translation position relative to the distal handle 30. The suture tension further assists in maintaining the inner shaft 26 rotational position as the proximal handle 32 is turned.

Figure 5:
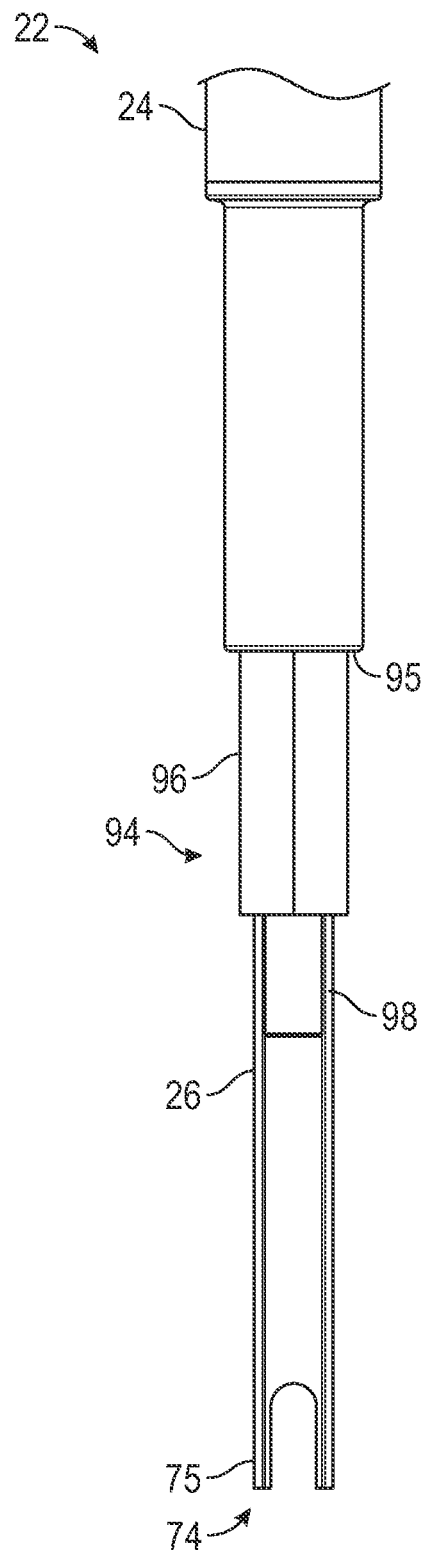
FIG. 5 illustrates a side view of a portion of the implant delivery device in accordance with an example of the disclosure.
Figure 6:
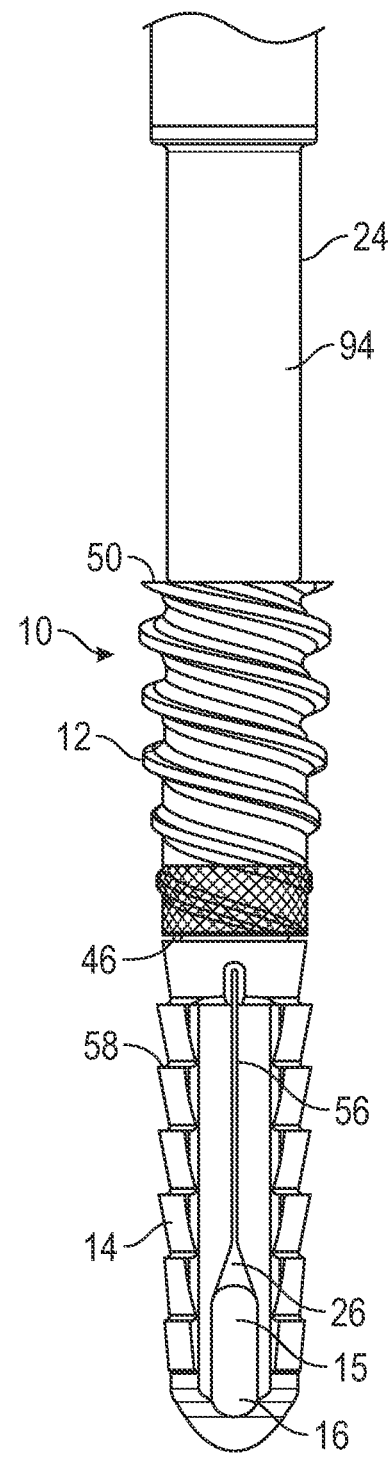
FIG. 6 illustrates the suture anchor mounted onto the portion of the implant delivery device in FIG. 5.

FIG. 5 illustrates further details of the implant delivery device 22 and FIG. 6 illustrates the suture anchor 10 mounted to the implant delivery device 22. As seen in FIG. 5, the cannulated outer shaft 24 includes the engagement portion 96 at the distal end 94 of the outer cannulated shaft 24. The inner shaft 26 extends through the outer cannulated shaft 24 and includes a forked end 75 at the distal end 74 of the inner shaft 26. The inner shaft 26 also includes an expanded portion 98 that is configured to form a press fit with a portion of the suture anchor 10. In one example, the expanded portion 98 includes two flats that mate with two flats on the inside of the distal member 14. However, other anti-rotational features between the expanded portion 98 and the suture anchor 10 can be used.

Referring to FIGS. 5 and 6, when the suture anchor 10 is mounted to the implant delivery device 22, the engagement portion 96 engages with the anti-rotational features 44 of the bore 36 of the anchor body 12 (see also FIG. 2B). Such that when rotational force is applied to the knob 33 of the proximal handle 32 (See FIG. 1), the rotational force is transferred to the anchor body 12 via the engagement portion 96 to rotatably drive the anchor body 12 into a bore via the threads 38 on the outer surface. Since the distal member 14 is rotatable relative to the anchor body 12, the distal member 14 does not rotate as the anchor body 12 is threadably implanted. The cannulated outer shaft 24 includes a shoulder 95, which can abut the proximal surface 50 of the anchor body 12 when the anchor body 12 is fully seated on the implant delivery device 22.

The expanded portion 98 of the inner shaft 26 is configured to engage a portion of the suture anchor 10. In one example, the expanded portion 98 forms a press fit with the distal member 14 within the coupling portion 21 of the distal member 14. The distal end 74 of the inner shaft 26 is extendable distally beyond the distal end 94 of the cannulated outer shaft 24 such that, when the distal end 94 the cannulated outer shaft 24 is engaging the proximal surface 50 of the anchor body 12, the distal end 74 of the inner shaft 26 is extendable through the anchor body 12 to a distance beyond the distal end 46 of the anchor body 12 to engage the suture located within the eyelet 16. The distal end 74 including the forked end 75 allows the sutures to be retained distally within the distal member 14 until anchor body 12 is rotationally inserted. The forked end 75 maintains the position of the sutures and prevents the sutures from entering the slot 56 too early. During advancement of the suture anchor 10, the outer shaft 24 advances over the inner shaft 26 at the same rate as the suture anchor 10 is advanced into the bone hole thereby allowing the suture 20 to enter the slot 56 without over tensioning. This is due to the threads 89 of proximal handle 32 mating with slots 86 of the distal handle 30, while the clip 78 locks translation of the inner shaft 26.

Thus, the anchoring system is configured such that the suture can be tensioned at a location within a bore distal from the anchor body 12 before the anchor body 12 is fully implanted within the bore. This allows for better and easier implants and allows a surgeon to have the desired tension in the suture before the anchor is implanted.

Methods of implanting the suture anchor 10 and performing a soft-tissue repair using the suture anchor 10 will now be disclosed. The methods set forth below are merely exemplary, and although certain steps may be set forth in a particular order, the order is not required and steps may be performed in a different order than set forth. The particular method below, used merely as an example, is a rotator cuff repair. It is contemplated, however, that suture anchor 10 can be used in any repair where soft tissue is to be drawn back to its natural condition in the body.

In an example, the method comprises first establishing an access portal through the skin and tissue of a shoulder of the patient (e.g., using a percutaneous cannula). Again, other anatomical locations are contemplated, such as repairs in the knee, hips, ankles, or other small bones. With the access portal established, one or more sutures can be passed through the access portal to the surgical site and through the soft tissue, in this case the rotator cuff in the patient's shoulder. The one or more sutures can be inserted through the soft tissue at one or more locations. As an example, a suture can be placed through the soft tissue at various locations. Many other suture configurations are possible, including where multiple sutures are used, such as the suture configurations used for trans-osseous equivalent.

FIGS. 7-12 illustrate using the anchoring system. Free ends of the sutures can be withdrawn from the access portal and threaded through the eyelet 16 of suture anchor 10 using suitable instrumentation, such as a loop of material used as suture threader. With free ends of the sutures 20 through the eyelet 16, the surgeon can then grasp free ends and insert suture anchor 10 through the access portal using implant delivery device 22.

Figure 7:
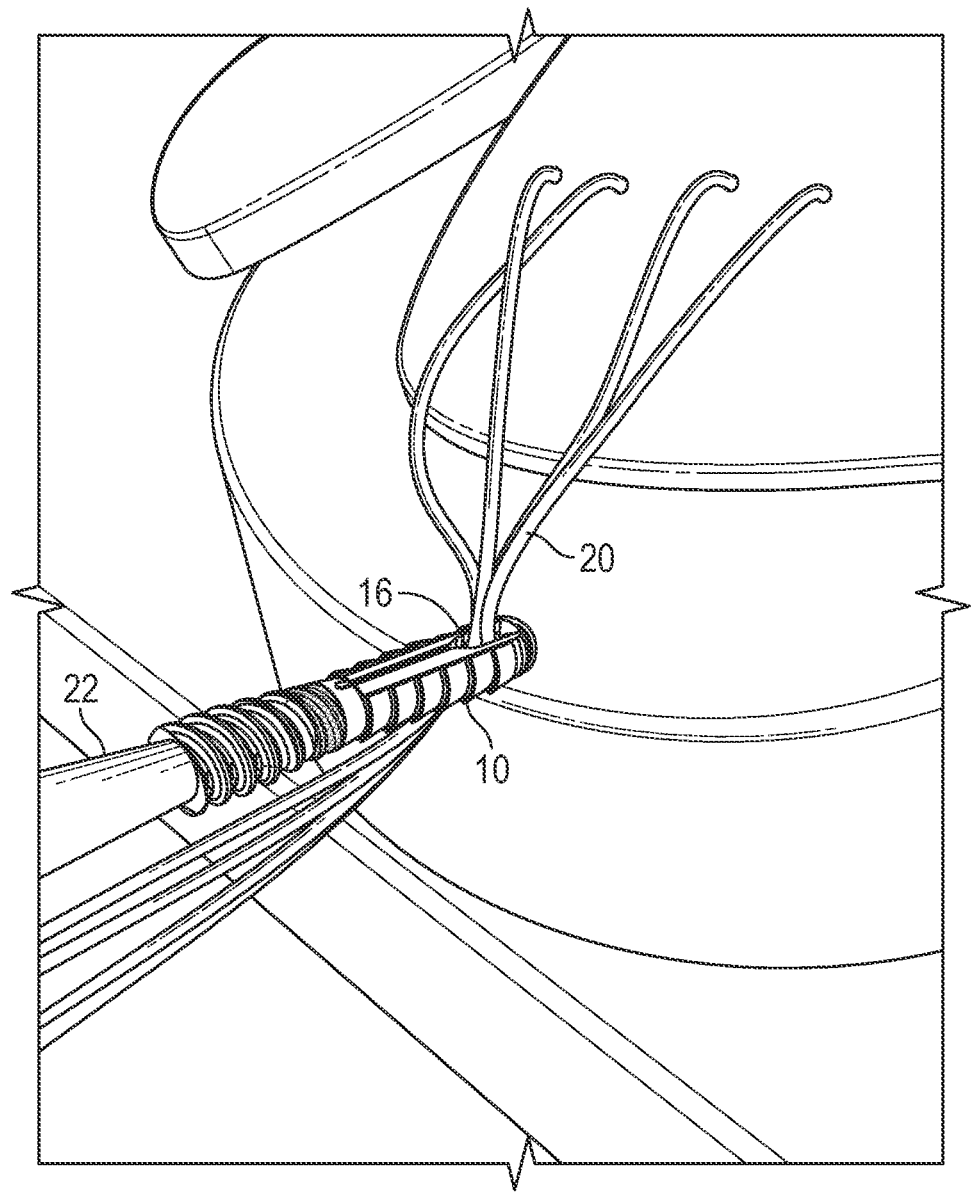
FIG. 7 illustrates a perspective view of the suture anchor being inserted in accordance with an example of the disclosure.

As seen in FIG. 7, the suture anchor 10 is attached to the implant delivery device 22 and the free ends of the sutures 20 extend through the eyelet 16. Suture anchor 10 can be pre-attached to the implant delivery device 22 or the surgeon can attach suture anchor 10 to the implant delivery device 22 before or after free ends of sutures 20 are drawn through the eyelet 16. The surgeon can then grasp free ends of the sutures 20 and use the implant delivery device 22 to insert suture anchor 10 through the access portal into the patient's shoulder.

Figure 8:
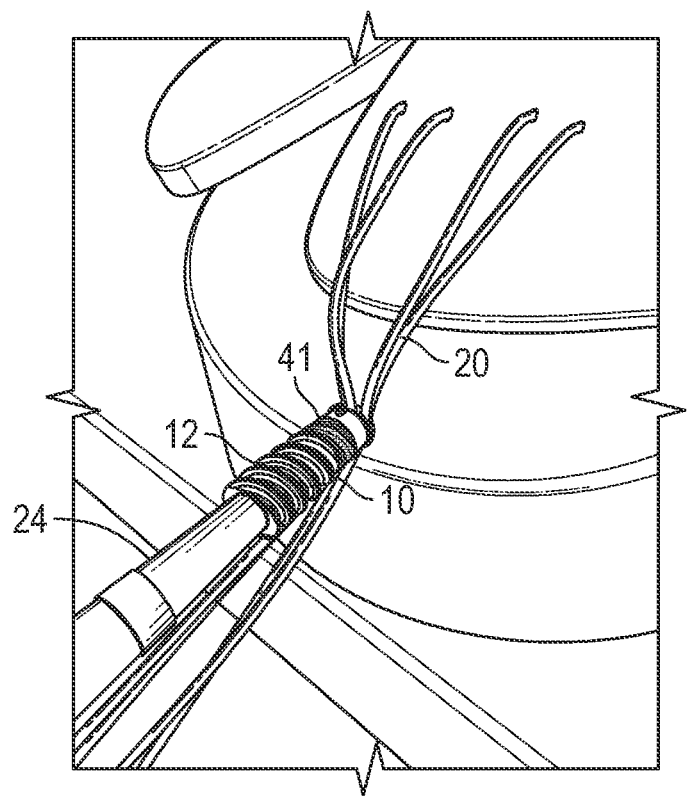
FIG. 8 illustrates a perspective view of the suture anchor being inserted in accordance with an example of the disclosure.
Figure 9:
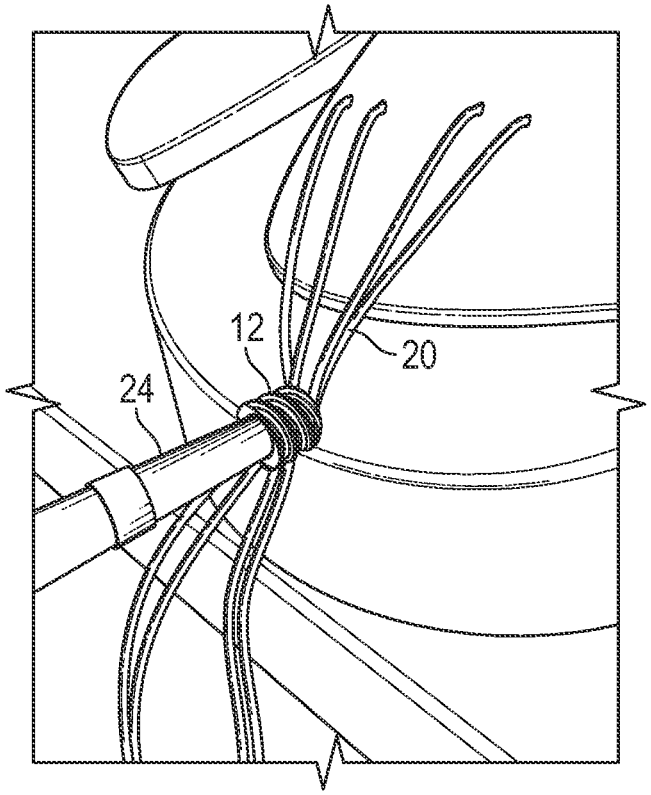
FIG. 9 illustrates a perspective view of the suture anchor being inserted in accordance with an example of the disclosure.
Figure 10:
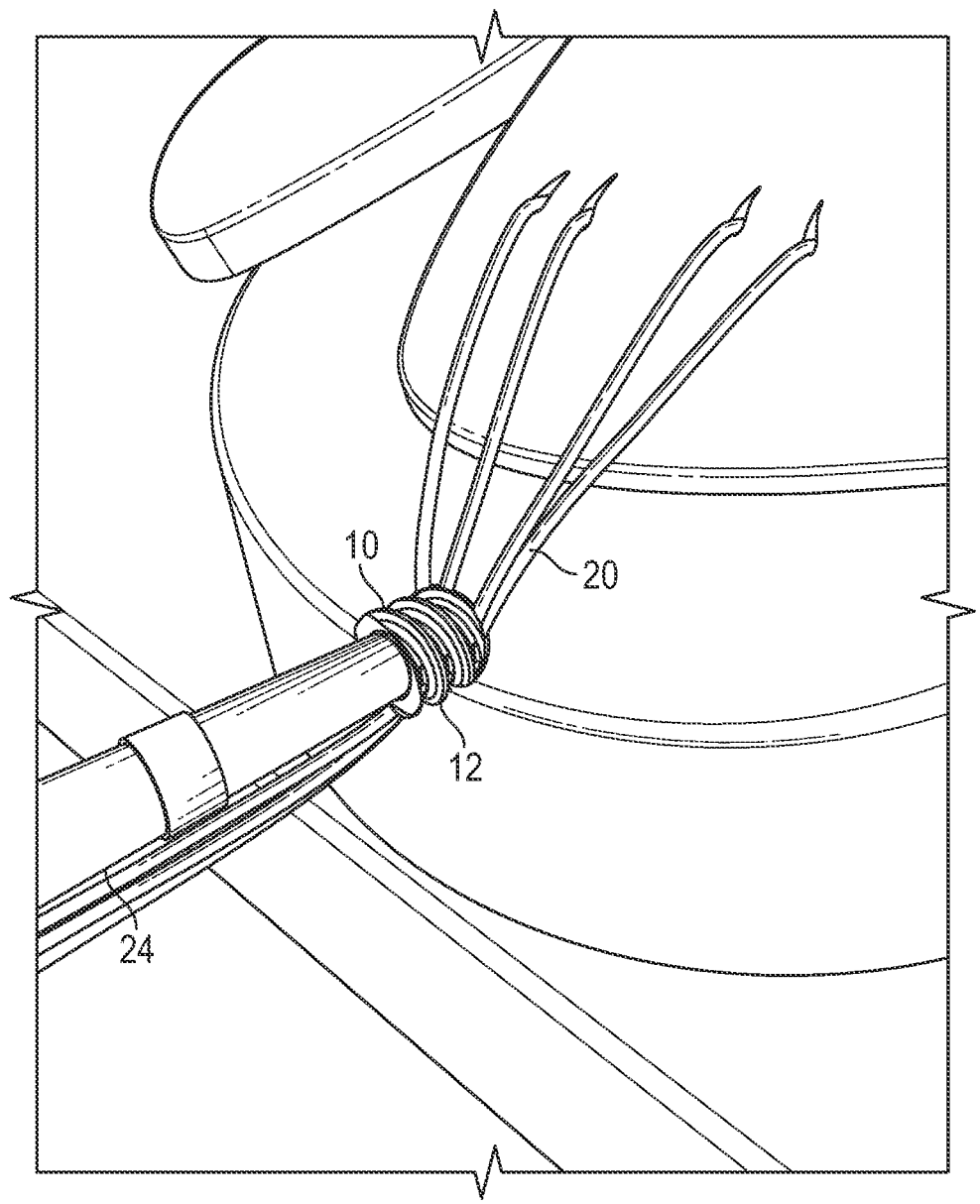
FIG. 10 illustrates a perspective view of the suture anchor being inserted in accordance with an example of the disclosure.
Figure 11:
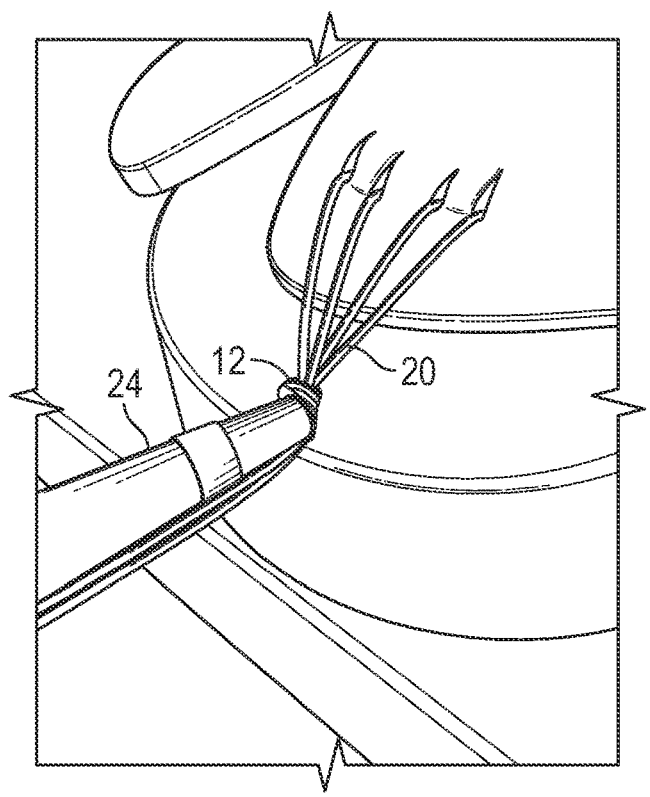
FIG. 11 illustrates a perspective view of the suture anchor being inserted in accordance with an example of the disclosure.
Figure 12:
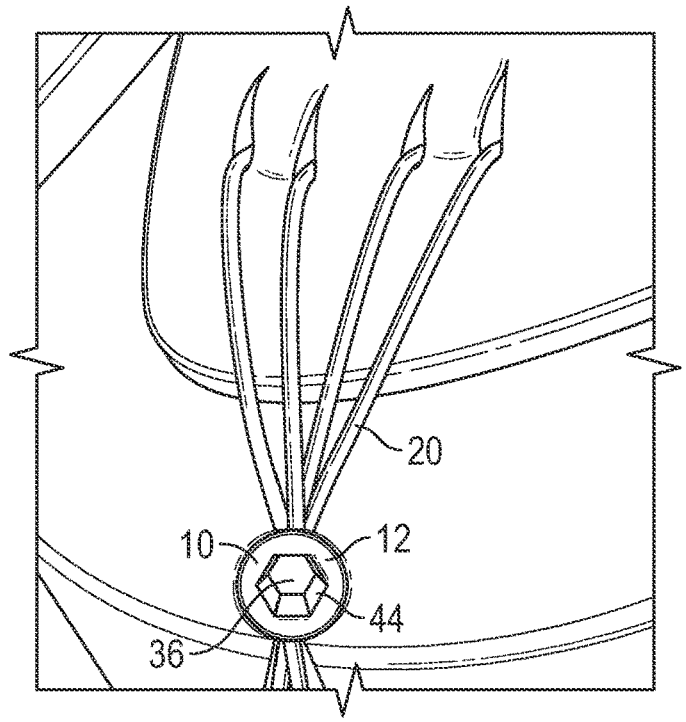
FIG. 12 illustrates a perspective view of the suture anchor being inserted in accordance with an example of the disclosure.

Previously, or at any point before suture anchor 10 is driven into bone, a suitable awl, pilot drill, or other instrument can be used by the surgeon to create an opening in bone of the patient for receiving suture anchor 10. The prepared hole is located with the tip of the suture anchor 10. FIGS. 8 and 9 illustrate the suture anchor 10 being advanced into the prepared hole. As discussed with respect to FIGS. 2A-C, the anchor body 12 includes an etch mark 41 that is an indication of when the sutures 20 may be tensioned. For example, FIG. 9 illustrates when the etch mark 41 is at or below the bone surface and the sutures 20 may be individually tensioned. For example, free ends of the sutures 20 can be tensioned by the surgeon to remove slack. FIG. 10 illustrates the sutures 20 after they have been tensioned. As discussed, the cleats 81 of the suture grasper section 83 may be used to manage the sutures after tensioning. At this point, the inner shaft 26 is at the same position. Simultaneously, as the knob 33 is rotated to insert the anchor body 12, the sutures 20 enter the slot 56 and the press fit is between the suture anchor 10 and the inner shaft 26 is released.

It should be noted that suture anchor 10 can be designed to allow tension to be applied to free ends of the sutures 20 when the suture anchor 10 is inserted in bone when the etch mark 41 is at or below the bone surface. Thus, there can be room between the walls of the bone hole and the suture anchor 10 of suture anchor to allow tensioning of the free ends and movement of the suture or sutures relative to the suture anchor 10 (e.g., before they move from the eyelet 16 into the slot 56.

After additional tension is applied to free ends by the surgeon, and because a tissue-engaging side of the sutures 20 can be engaged with soft tissue, sutures 20 extending through the suture anchor 10 can move from the eyelet 16 into the slot 56 when the knob 33 is rotated and the anchor body 12 is inserted by rotation. For example, as the knob 33 is rotated, the cannulated outer shaft 24 moves distally relative to the inner shaft 26 and "pushes" or moves the suture anchor 10 distally such that the expanded portion 98 disengages from the distal member 14 of the suture anchor 10 and the slot 56 moves distally over sutures 20 engaging them in the slot 56.

Once the sutures 20 are tensioned, the suture anchor 10 can be further advanced into the hole. For example, referring to FIGS. 1A, 4A, and 11, a surgeon can apply slight downward pressure to the distal handle 30 while turning the knob 33 of the proximal handle 32 in a clockwise direction to advance the threaded anchor body 12 of the suture anchor 10. As the knob 33 is turned, the rotational force is transmitted to the anchor body 12 of the suture anchor 10 such that the proximal handle 32, the cannulated outer shaft 24, and the anchor body 12 rotate about a longitudinal axis, while the inner shaft 24, the distal member 14, and the distal handle 30 remain at fixed rotational position (i.e., they do not rotate because of the tension on the sutures 20). The surgeon will continue to rotate the knob 33 until the suture anchor 10 is fully seated.

Once fully seated, the surgeon can remove the implant delivery device 22 by pulling backwards on the implant delivery device 22, e.g., the handle portion 28, and withdraw the implant delivery device 22 from the suture anchor. Additionally, the surgeon can trim any excess suture material resulting from free ends of the sutures 20 extending outside of the bone hole. The repair can then be completed.

In the devices shown in the figures, particular structures are shown as being adapted for use as a suture anchor or in a method of implantation thereof. The disclosure also contemplates the use of any alternative structures for such purposes. For example, the distal member 14 is shown having a closed end, however, the distal member 14 could have an open end. The anchor body and distal member can include various advancement/fixation means such as barbs, projections, threads, grooves, ridges, etc. The coupling between the distal member and the anchor body is shown as the distal member being inserted into the anchor body. However, other coupling mechanisms can be used, e.g., a portion of the anchor body being inserted into the distal member. Additionally, instead of applying tension after the suture anchor is advanced to the etch line (discussed herein), tension on the sutures could be applied prior to insertion of the suture anchor 10 into the bone hole and maintained during insertion so that the surgeon does not need to apply additional tension to the sutures. Further, room between the walls of the bone hole and the suture anchor 10 allows for sutures on the non-tissue side to move so that the tissue is not over tensioned.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

VARIOUS NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An anchoring system, comprising:
   a suture anchor configured for insertion into a bore formed in a bone, the suture anchor including:
      an anchor body including a threaded outer surface, an etch line, a bore extending from a proximal end of the anchor body to a distal end of the anchor body, and a stop surface located within the bore and spaced proximally from the distal end of the anchor body; and
      a distal member that is rotatable relative to the anchor body about a longitudinal suture anchor axis, the distal member having an aperture that traverses the distal member, the aperture including an eyelet and a slot, the eyelet and the slot being sized to permit a suture to traverse the distal member, wherein a length of the slot is greater than a length of the anchor body from the proximal end of the anchor body to a proximal end of the etch line to prevent over tensioning of the suture during implantation of the suture anchor, wherein the distal member includes a projection extending from a proximal end thereof, the projection including a lip, a shoulder spaced distally from the lip, and a lumen configured for receipt of a delivery device, wherein upon assembly of the anchor body to the distal member, the lip engages the stop surface within the bore and the shoulder engages the distal end of the anchor body, and wherein the distal member includes an outer surface including a plurality of fixation projections configured to provide an outward force sufficient to prevent the suture anchor from backing out of the bore after insertion.

2. The anchoring system of claim 1, wherein the slot has a first slot end positioned toward the proximal end of the distal member and a second slot end positioned adjacent to the eyelet.

3. The anchoring system of claim 2, wherein the eyelet extends from a first eyelet end adjacent to the second slot end to a second eyelet end positioned adjacent to a distal end of the distal member.

4. The anchoring system of claim 3, wherein the slot and the eyelet are in fluid communication with each other and the first slot end is a closed end.

5. The anchoring system of claim 1, wherein the aperture defines first and second openings in first and second sides of the distal member through which the suture can extend.

6. The anchoring system of claim 1, wherein a maximum dimension of the eyelet is greater than a maximum dimension of the slot.

7. The anchoring system of claim 1, wherein the eyelet includes a transition region that permits movement of the suture from the eyelet to the slot.

8. The anchoring system of claim 1, wherein the distal member includes a suture body portion and a coupling portion, the coupling portion including the projection.

9. The anchoring system of claim 8, wherein the distal member includes a blind bore extending from the coupling portion and terminating within the suture body portion.

10. The anchoring system of claim 1, further includes:
    an implant delivery device, including:
       a handle portion; and
       a drive shaft portion, including:
          a cannulated outer shaft, the cannulated outer shaft configured to engage the proximal end of the anchor body for driving the suture anchor into the bore; and
          a suture pulley shaft portion, including:
             an inner shaft slidably received in the cannulated outer shaft, wherein a distal end of the inner shaft is extendable distally beyond a distal end of the cannulated outer shaft such that, when the cannulated outer shaft is engaging the proximal end of the anchor body, the distal end of the inner shaft is extendable through the anchor body to a distance beyond the distal end of the anchor body to engage with the distal member to rotationally lock the distal member to the inner shaft.

11. The anchoring system of claim 10, wherein, when the suture is tensioned, the tension rotationally locks the inner shaft and the distal member relative to the cannulated outer shaft and the anchor body.

12. The anchoring system of claim 10, wherein the inner shaft includes a fork on the distal end of the inner shaft.

13. The anchoring system of claim 12, wherein the fork is a two-pronged fork.

14. The anchoring system of claim 10, wherein the anchoring system is configured so that the suture is at a proper location to be tensioned when the distal end of the inner shaft is on a bottom surface of the bore and holding the suture at a distal position of the bore.

15. An anchoring system, comprising:
    a suture anchor configured for insertion into a bore formed in a bone, the suture anchor including:
       an anchor body defining a bore extending from a proximal end of the anchor body to a distal end of the anchor body; and
       a distal member that is rotatable relative to the anchor body about a longitudinal suture anchor axis and translationally fixed relative to the anchor body along the longitudinal suture anchor axis, the distal member including a projection at a proximal end thereof, the projection including a lip, a shoulder spaced distally from the lip, and a lumen extending through the projection and configured for receipt of a delivery device, wherein upon assembly of the anchor body to the distal member, the lip engages a stop surface within the bore and the shoulder engages the distal end of the anchor body;
       the anchor body including a threaded outer surface, an etch line, and a plurality of fenestrations extending through the threaded outer surface and configured to receive at least one of bone or tissue during insertion and to assist with osseointegration as the bone heals around the suture anchor, the distal member having an aperture that traverses the distal member, the aperture including a slot and an eyelet, wherein a length of the slot is greater than a length of the anchor body from the proximal end of the anchor body to a proximal end of the etch line to prevent over tensioning of a suture during implantation of the suture anchor, and wherein an outer surface of the distal member includes a plurality of fixation projections configured to provide an outward force sufficient to prevent the suture anchor from backing out of the bore after insertion; and an implant delivery device, including:
a handle portion;
a drive shaft portion, including:
a cannulated outer shaft, the cannulated outer shaft configured to engage the proximal end of the anchor body for driving the suture anchor into a bore; and
a suture pulley shaft portion, including:
an inner shaft slidably received in the cannulated outer shaft, wherein a distal end of the inner shaft is extendable distally beyond a distal end of the cannulated outer shaft such that, when the cannulated outer shaft is engaging the proximal end of the anchor body, the distal end of the inner shaft is extendable through the anchor body to a distance beyond the distal end of the anchor body to engage with the distal member to rotationally lock the distal member to the inner shaft.

16. The anchoring system of claim 15, wherein a portion of the bore havinghas an anti-rotational shape.

17. The anchoring system of claim 15, wherein the inner shaft includes a fork on the distal end of the inner shaft.

18. A method for securing a suture to a bore, comprising:
passing a suture through soft tissue of a patient and through an eyelet of a suture anchor, the suture anchor including:
an anchor body and a distal member that is rotatable relative to the anchor body about a longitudinal suture anchor axis, the anchor body extending from a proximal end to a distal end and including a threaded outer surface, an etch line, a bore extending from the proximal end of the anchor body to the distal end of the anchor body, and a stop surface located within the bore and spaced proximally from the distal end of the anchor body, the distal member including an aperture including the eyelet and a slot, wherein a length of the slot is greater than a length of the anchor body from the proximal end of the anchor body to a proximal end of the etch line to prevent over tensioning of the suture during implantation of the suture anchor, the distal member further including a projection extending from a proximal end thereof, the projection including a lip, a shoulder spaced distally from the lip, and a lumen configured for receipt of a delivery device, wherein upon assembly of the anchor body to the distal member, the lip engages the stop surface within the bore and the shoulder engages the distal end of the anchor body, and wherein the distal member includes an outer surface including a plurality of fixation projections configured to provide an outward force sufficient to prevent the suture anchor from backing out of a bore after insertion;

coupling a delivery device to the suture anchor, including inserting a shaft of the delivery device through the lumen of the projection on the distal member;

positioning the suture anchor at a bore so that a portion of the suture distally past the distal end of the anchor body is located at or near a bottom of the bore while the anchor body is above the bore;

advancing the suture anchor until a portion of the anchor body is within the bore such that the etch line is at or below a proximal end of the bore;

tensioning a free end of the suture; and rotating the anchor body via a handle of the delivery device to advance the suture anchor into the bore to secure the suture, wherein the anchor body rotates relative to the distal member such that, as the anchor body rotates, a rotational position of the distal member is maintained during insertion.

\* \* \* \* \*